(12) United States Patent
Hynynen et al.

(10) Patent No.: US 7,674,229 B2
(45) Date of Patent: Mar. 9, 2010

(54) ADAPTIVE ULTRASOUND DELIVERY SYSTEM

(75) Inventors: Kullervo Hynynen, Medfield, MA (US); Nathan McDannold, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 87 days.

(21) Appl. No.: 11/370,094

(22) Filed: Mar. 7, 2006

(65) Prior Publication Data
US 2006/0241529 A1 Oct. 26, 2006

Related U.S. Application Data

(60) Provisional application No. 60/659,207, filed on Mar. 7, 2005.

(51) Int. Cl.
*A61H 1/00* (2006.01)
(52) U.S. Cl. .................. 600/439; 600/437; 424/9.1; 601/2
(58) Field of Classification Search .................. 601/2–4; 600/437, 439
See application file for complete search history.

(56) References Cited

U.S. PATENT DOCUMENTS

| | | | |
|---|---|---|---|
| 5,752,515 A * | 5/1998 | Jolesz et al. ................ 600/458 |
| 6,514,221 B2 | 2/2003 | Hynynen et al. | |
| 6,575,969 B1 * | 6/2003 | Rittman et al. ................ 606/41 |
| 6,733,450 B1 * | 5/2004 | Alexandrov et al. ........ 600/439 |
| 2004/0049134 A1 * | 3/2004 | Tosaya et al. ................... 601/2 |
| 2004/0122323 A1 * | 6/2004 | Vortman et al. ............. 600/459 |
| 2005/0020945 A1 * | 1/2005 | Tosaya et al. ................... 601/2 |
| 2005/0084538 A1 * | 4/2005 | Dayton et al. ............... 424/489 |
| 2006/0058708 A1 * | 3/2006 | Heart et al. ..................... 601/2 |
| 2006/0184070 A1 * | 8/2006 | Hansmann et al. ............. 601/2 |
| 2007/0073197 A1 * | 3/2007 | Prausnitz et al. ............... 601/2 |
| 2007/0083120 A1 * | 4/2007 | Cain et al. ................... 600/439 |
| 2007/0299370 A1 * | 12/2007 | Bystritsky ....................... 601/2 |
| 2008/0221382 A1 * | 9/2008 | Karshafian et al. ............. 600/2 |

OTHER PUBLICATIONS

N McDannold, N Yykhodtseva, K Hynynen. Targeted disruption of the blood-brain barrier with focused ultrasound. 2005 IEEE Ultrasonics Symposium: pp. 1249-1252.*

(Continued)

*Primary Examiner*—Brian Casler
*Assistant Examiner*—Amanda Lauritzen
(74) *Attorney, Agent, or Firm*—Fish & Richardson P.C.

(57) ABSTRACT

A method and system for opening a blood-brain barrier are described. Ultrasonic radiation having a frequency below 500 kHz is directed through a skull to a target region and the frequency is adjusted such that wavefronts of the ultrasonic radiation remain essentially unchanged while passing through the skull.

25 Claims, 5 Drawing Sheets

OTHER PUBLICATIONS

Graham-Rowe, D. A new method of getting drugs into the brain: focused ultrasound waves can make a tiny, temporary hole in the barrier surrounding the brain. MIT Technology Review online publication. Jun. 13, 2006.*

Reymond, E. Drug delivery breakthrough for brain tumour therapy. in-pharmatechnologist.com online publication. Oct. 31, 2006.*

N McDannold, N Vykhodtseva, S Raymond, FA Jolesz, K Hynynen. MRI-guided targeted blood-brain barrier disruption with focused ultrasound: histological findings in rabbits. Ultrasound in Med and Biol: 31(11) pp. 1527-1537, 2005.*

AH Mesiwala, PD Mourad. Letters to the Editor: Monitoring of biological effects of focused ultrasound beams on the brain. Dept of Neurological Surgery, University of Washington School of Medicine. Radiology 2002; 224: 294-297.*

K Hynynen, N McDannold, N Vykhodtseva, FA Jolesz. Noninvasive MR Imaging-guided focal opening of the blood-brain barrier in rabbits. Radiology, 2001; 220:640-646.*

NI Vykhodtseva, K Hynynen, C Damianou. Histologic effects of high intensity pulsed ultrasound exposure with subharmonic emission in rabbit brain in vivo. Ultrasound in Medicine and Biol, 21(7): 969-979.*

International Search Report for Application No. PCT/US06/08194.

Written Opinion for Application No. PCT/US06/08194.

Barnett S., Nonthermal issues: Cavitaion-Its nature, detection and measurement. Ultrasound in Medicine & Biology. Jun. 1998, vol. 24 Supplement 1, pp. S11-S21.

Hynynen K., et al. Noninvasive MR Imaging-guided Focal Opening of the Blood-Brain Barrier in Rabbits. Radiology. 2001. vol. 220, pp. 640-646.

Sokka S.D., et al. MRI-guided gas bubble enhanced ultrasound heating in vivo rabbit thigh. Phys. Med. Biol. 2003, vol. 48, pp. 223-241.

Pitt W.G., et al. Ultrasonic Drug Deliver—A General Review. Expert Opin Drug Deliv. Nov. 2004, vol. 1, No. 1, pp. 37-56 (32 pages).

* cited by examiner

ADAPTIVE ULTRASOUND DELIVERY SYSTEM

CROSS-RELATED APPLICATION

Under 35 U.S.C. 119(e)(1), this application claims the benefit of provisional application Ser. No. 60/659,207, filed Mar. 7, 2005.

TECHNICAL FIELD

This invention relates to medical applications of ultrasound, and more particularly to a system for delivering ultrasound.

BACKGROUND

The blood-brain barrier (BBB) is a specialized system of capillary endothelial cells that inhibits certain substances in the blood stream from reaching the brain. While the BBB may protect the brain from harmful substances present in the blood stream, it may also prevent or severely delay the transport of therapeutic or diagnostic substances to the brain. Consequently, many drugs that are potentially useful for treating or diagnosing brain ailments cannot be administered through the blood because they cannot pass through the BBB.

Various techniques for delivering therapy to the brain thus begin with the opening of the BBB before administering a drug into the blood stream. One such technique uses ultrasound-induced cavitation to open the BBB. As the name suggests, ultrasound-induced cavitation is a process in which ultrasonic radiation causes bubbles to form and grow in a target region adjacent to where a drug is to be delivered through the BBB. The ultrasonic radiation is applied until the bubbles reach a condition that induces an opening in the BBB. Such ultrasound-induced cavitation events via transcranial exposure may have other therapeutic or diagnostic applications in the brain as well.

The foregoing technique involves focusing the ultrasound at the correct target region. Imaging techniques, such as magnetic-resonance imaging (MRI) or computed tomography (CT), are used to guide the ultrasound to the target tissue and to monitor the BBB. The opening of the BBB may be detected by evaluating MRI or CT images of the target region.

SUMMARY

The invention provides methods and systems for ultrasound deliver.

In one aspect, a method for opening a blood-brain barrier includes directing, through a skull, ultrasonic radiation having a frequency below 500 kHz to a target region. The ultrasonic radiation has a frequency selected to open the blood-brain barrier at the target region. The frequency is adjusted such that wavefronts of the ultrasonic radiation remain essentially unchanged while passing through the skull.

In another aspect, a system for opening a blood-brain barrier includes an ultrasound source that directs ultrasonic radiation having a frequency below 500 kHz to a target region through a skull, the ultrasonic radiation having a frequency selected to open the blood-brain barrier at the target region and having a wavelength that is longer than irregularities of the skull whose effect on wavefronts of the ultrasonic radiation is to be suppressed. Examples of irregularities include bumps, indentations, and curvature anomalies of the skull. The system also includes a controller for controlling a focal region of the ultrasound relative to the target region without compensating for distortion of the focal region caused by the ultrasonic radiation passing through the irregularities of the skull.

Implementations may include one or more of the following features. The frequency may be selected to have a wavelength that is longer than those irregularities of the skull whose effect on the wavefronts is to be suppressed. For example, the frequency may be lowered until a shape and location of the focal region conforms to a shape and location of the target region. The ultrasonic radiation generated from the ultrasound source may have a frequency between 100 kHz and 400 kHz (e.g., at a frequency of 250 kHz), a time averaged power of approximately 10 mW, and a pressure amplitude of approximately 0.3 MPa within a focal region. The ultrasonic radiation may be generated using an array of ultrasound transducers. Such an array may be configure to have fewer than 5000 ultrasound transducers (e.g., 1000 ultrasound transducers) and to cover the whole skull or a portion of the skull.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and the accompanying figures.

DETAILED DESCRIPTION

Figure 1:
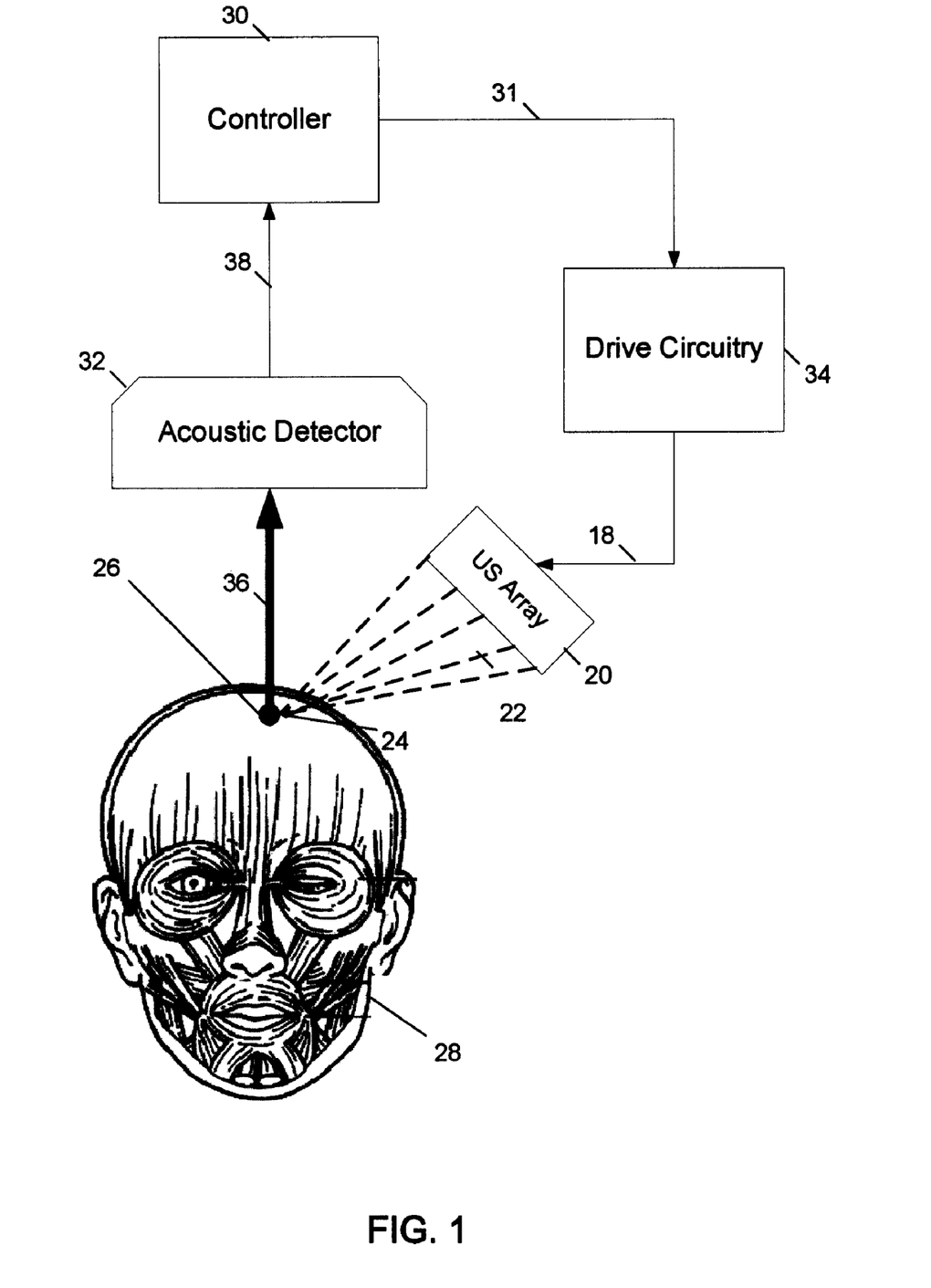
FIG. 1 shows a block diagram of a system for the delivery of ultrasound into the brain.

FIG. 1 shows a block diagram of a feedback-control system 10 for opening the blood-brain barrier (BBB) 26 at a target region 24 in the brain of a patient 28. Such a system can be used for other medical applications of ultrasound, for example tissue ablation, thrombolysis, etc. The system 10 includes an ultrasound array 20 focused at a focal region, drive circuitry 34 for driving the array 20, an acoustic detector 32 for receiving acoustic emissions 36 from the target region 24, and a controller 30 for adaptively controlling the location of the focal region relative to the target region 24 by providing control signals 31 to the drive circuitry 34 in response to acoustic data 38 provided by the acoustic detector 32. The acoustic data 38 collected from the acoustic detector 32 is used to determine whether or not the BBB 26 has opened.

Ultrasonic radiation 22 is directed from the ultrasound array 20 to a target region 24 within the brain 26. The ultrasonic radiation 22 stimulates the formation of gaseous bubbles at the target region 24 and causes the bubbles to expand. Alternatively, the ultrasonic radiation 22 can cause oscillation of bubbles that have been injected into the blood stream and delivered to the target region 24. The strength and frequency of the ultrasonic radiation 22 may be adjusted such that the gaseous bubbles reach a resonant size at which the bubbles oscillate. The ultrasonic radiation may also be adjusted to cause the bubbles to collapse or burst. The expansion, oscillation, and bursting of the bubbles cause acoustic emissions 36 that characterize the sizes and conditions of the bubbles. Thus, if bubbles of a certain condition (e.g., oscillating bubbles) or combination of conditions (e.g., some bubbles bursting and some bubbles oscillating) are known to induce BBB opening, the acoustic emissions 36 may be correlated with the opening of the BBB 26. The acoustic emission 36 may also allow identification, monitoring, and control of other end points of a procedure, such as tissue ablation and thrombolysis.

An acoustic detector 32 collects acoustic emissions 36 and converts those emissions 36 into electrical signals. The acoustic detector 32 may be any device that converts acoustic energy to electrical signals. For example, the acoustic detector 32 may be a directional or omnidirectional hydrophone, or an ultrasound transducer configured as a receiver. The acoustic detector 32 could also be one that relies on optical methods for detecting acoustic emissions 36. The acoustic detector 32 may be of any appropriate size and shape. For example, the acoustic detector 32 could be configured as a ring that surrounds an ultrasound transmitter. The acoustic detector could also be an imaging device (ultrasound, optical, CT, MRI, etc.) that detects the acoustic emissions 36 or their byproducts.

From the acoustic data 38, the controller 30 determines whether or not the desired endpoint has been reached, for example, whether the BBB 26 has been opened. To do so, the controller 30 may analyze the spectrum of the acoustic signal. For example, the controller may determine that the BBB 26 has opened upon detecting emissions at a given frequency or in a given frequency range. Such emissions may include wideband and subharmonic emissions. To detect the opening of the BBB 26, the controller 30 may also analyze a change in the strength of various harmonic frequencies of the acoustic spectrum. For example, enhancement of a harmonic (e.g., second harmonic) or a set of harmonics (e.g., second and third harmonics) of subharmonic emissions may indicate the opening of the BBB 26. From the acoustic data 38, the controller 30 may also determine a distribution of bubble oscillations or bursts that is indicative of the opening of the BBB 26.

The controller 30 identifies the target region 24 using an ultrasound echo mapping process described below. The controller may identify the target region 24 in real-time. After the target region 24 has been identified, the controller 30 calculates control signals 31 that focus the ultrasonic radiation 22 at the target region 24. Such control signals 31, may be derived from, for example, amplitudes and phases that cause the ultrasound array 20 to illuminate a focal region that overlaps the target region 24. The controller 30 then sends the control signals 31 to the drive circuitry 34. In response to the control signals 31, the drive circuitry 34 generates drive signals 18 that cause the ultrasound array 20 to focus ultrasonic radiation 22 at the target region 24. While the tissue is undergoing sonication, the acoustic detector 32 receives acoustic emissions 36 and sends a corresponding stream of acoustic data 38 to the controller 30. Using the acoustic data 38, the controller 30 monitors any movement of the focal region relative to the target region 24, tracks and adaptively controls the progress of the sonication, and determines whether or not the BBB 26 has opened. The amplitude, burst length, burst repetition frequency, and/or frequency distribution of the ultrasonic radiation 22 are controlled to cause the bubbles to grow to their resonant sizes and/or burst without damaging any surrounding neural tissue. In one implementation, the ultrasonic radiation 22 has a time averaged power of 10 mW and a pressure amplitude of 0.3 MPa within a focal region. The ultrasonic radiation 22 is applied as bursts of 1-100 ms long pulses at a 1 Hz repetition frequency for 20 seconds. The frequency of the ultrasonic radiation 22 can be as high as 1 MHz, though preferably the frequency is between 100 kHz and 400 kHz. As used herein, "low frequency" designates frequencies below 500 kHz and "high frequency" designates frequencies above 500 kHz.

Wavefronts of the ultrasonic radiation may be distorted as the waves pass through irregularities in the skull. Examples of irregularities include bumps, indentations, and curvature anomalies of the skull. These distortions in the wavefronts can cause the location and shape of the focal region to change so that it no longer conforms to the location and shape of the target region 24. To reduce such "focal distortion," low-frequency ultrasound rather than high-frequency ultrasound may be used. Because low frequency ultrasound has a longer wavelength than high frequency ultrasound, irregularities in the acoustic propagation path length caused by the shape of the skull are relatively small compared to the wavelengths when low frequency ultrasound is used. In particular, the distortion caused by skull irregularities is negligible for ultrasound frequencies between 100-400 kHz or lower. In some embodiments, the frequency is lowered until the shape and location of the focal region conforms to the shape and location of the target region.

In addition to reducing the focal distortion, using low frequency ultrasound has other advantages. An advantage stemming from reducing the focal distortion is that the control signals 31 are easier to calculate. For example, if the distortion is negligible, the controller 30 may calculate the control signals for controlling the location of the focal region of the ultrasound relative to the target region without compensating for distortion of the focal region. Using low frequency ultrasound is also advantageous because less power is inflicted on the patient 28 and less power is required from the ultrasound array 20.

Figure 2:
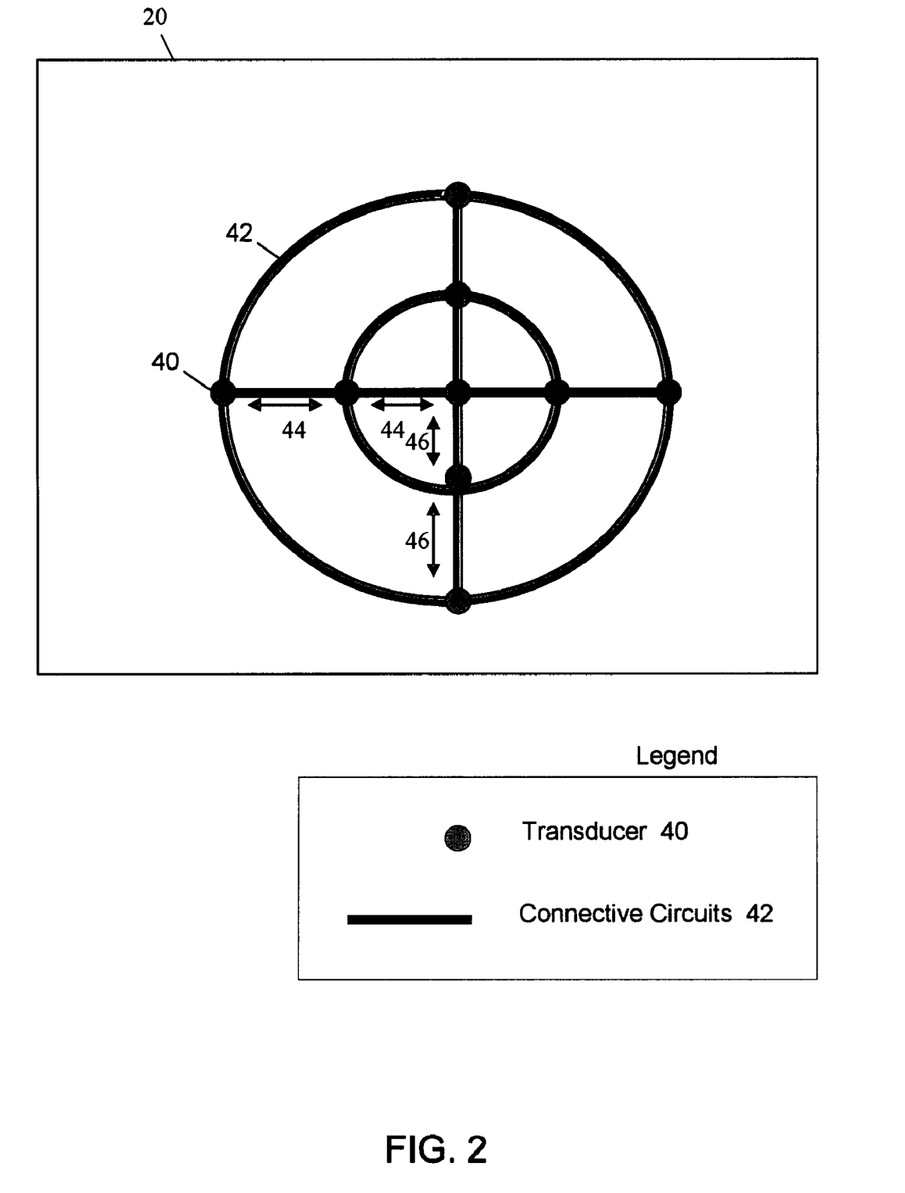
FIG. 2 shows a two-dimensional ultrasound phased array from the system of FIG. 1.

Referring to FIG. 2, in one embodiment, the array 20 is a two-dimensional ultrasound array having multiple transducers 40. The transducers 40 are connected to the driving electronics by connective circuits 42. Connective circuits 42 may include multilayer flexible circuits, micro-coaxial cables, and other types of connective circuits. Any number of transducers 40 could be arranged in any pattern, though a preferred arrangement has transducers 40 arranged in concentric circles in which the horizontal distances 44 and vertical spacings 46 between the centers of the transducers 40 are equal to half the wavelength of the ultrasonic radiation 22. However, larger spacings can also be used. The vertical and horizontal spacing between the centers of the transducers 40 could be equal, but different from one half of the wavelength of the ultrasonic radiation 22. Alternatively, the vertical and horizontal spacings could be unequal. The transducers 40 may also be arranged in a grid, a spiral, or an irregular pattern, though any arrangement of transducers 40 is possible. The array 20 may include transducers 40 all having the same size, shape, and material composition, or the array 20 may include any combination of transducers 40 of different sizes, shapes, and material compositions The array 20 may conform to any appropriate size or shape. For example, the array 20 may assume a hemispherical shape that surrounds a portion of the skull. The array 20 may also cover the entire skull. The number of transducers 40 may vary. High frequency ultrasound arrays typically contain approximately 5000 or more transducers 40, whereas low frequency arrays typically contain fewer than 5000 transducers. For example, a 250 kHz ultrasound array that covers the whole skull may contain approximately 1000 transducers 40. It is also possible to use a single or multiple focused ultrasound beams and mechanical movement of the transducer(s) 40 for the delivery of the ultrasonic radiation 22 to the target region 24.

Figure 3:
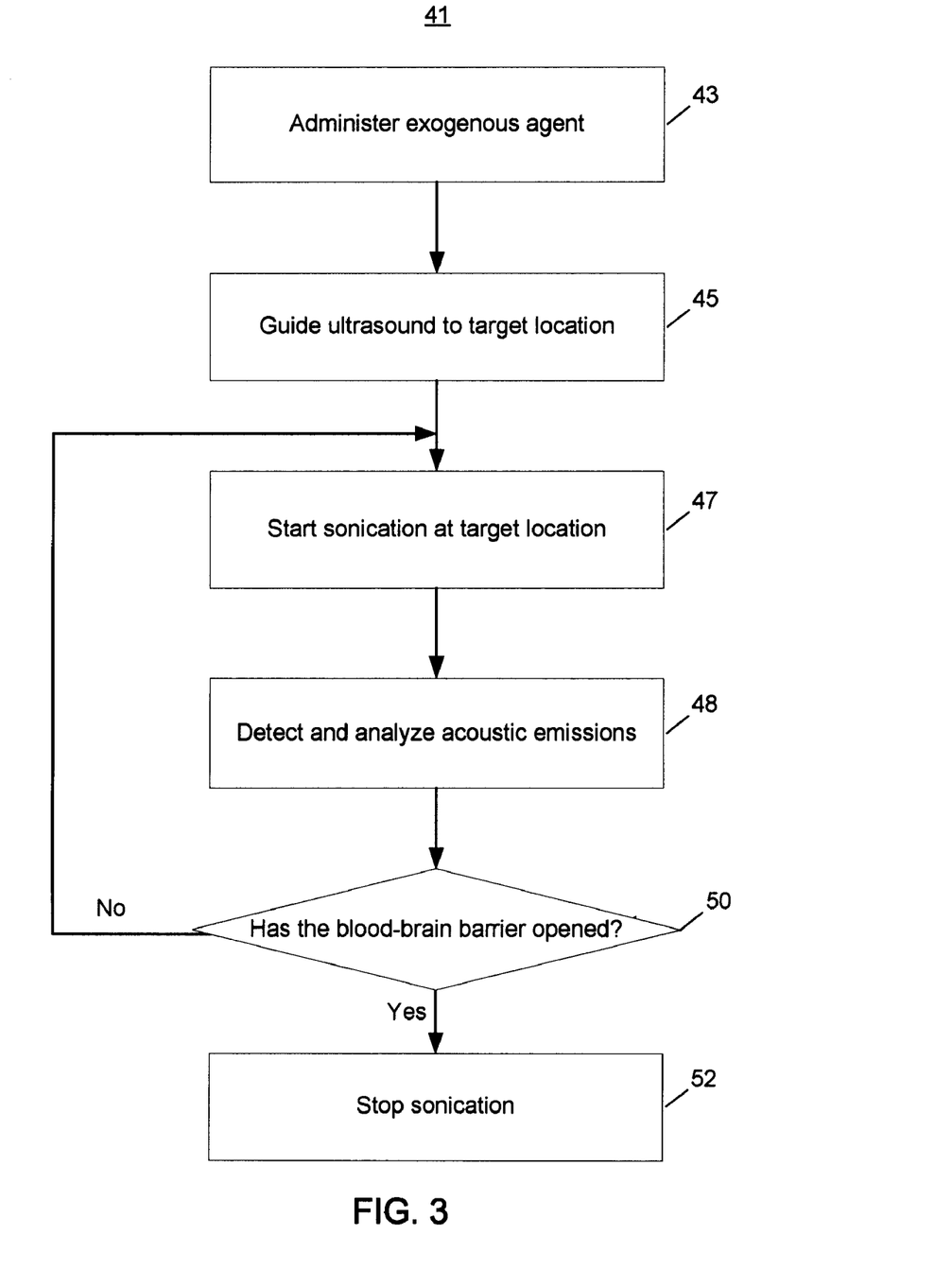
FIG. 3 is a flow chart of a process for opening the BBB using the system of FIG. 1.

FIG. 3 describes a treatment process 41 by which the system 10 is used to open the BBB 26 at a target region 24. One first administers an exogenous agent (step 43) to the patient 28. The agent may be a substance that contains preformed micro bubbles or a substance that forms bubbles when stimulated by ultrasound or other means or any other agent that interacts with the ultrasound in a desired way. The agent may be administered (step 43) orally or intravenously, or intra-arterially. One then waits long enough for the agent to reach the target region 24.

The focal region is then guided to the target region 24 (step 45) using an echo-image registration process that is described below. During the guiding procedure (step 45), the controller 30 calculates the distance between the target region 24 and the ultrasound array 20. The controller 30 also calculates the control signals 31 required to cause the array 20 to focus the ultrasonic radiation 22 at the target region 24. In response to control signals 31 from the controller 30, the drive circuitry 34 causes the ultrasound array 20 to start sonicating the target region 24 (step 47). Acoustic emissions 36 are detected and analyzed (step 48) to determine whether or not the BBB 26 has opened (step 50). The analysis and detection of the acoustic emissions 36 (step 48) may be performed simultaneously with the sonication (step 47). Alternatively sonication (step 47) and analysis (step 48) may be performed sequentially, with the sequence being repeated several times.

From the acoustic data 38 provided by the acoustic detector 32, the controller 30 determines whether or not the BBB 26 has opened (step 50). In one implementation, the opening of the BBB 26 is detected solely by analyzing acoustic data 38 and without using other diagnostic techniques, such as real-time MRI, CT, PET, or ultrasound imaging. In a second implementation, real-time MRI CT, PET, or ultrasound imaging techniques are used in combination with the acoustic data 38 to detect the opening of the BBB 26. If an opening in the BBB 26 has been detected, the controller 30 instructs the drive circuitry 34 to stop the sonication (step 52). However, if no BBB opening has been detected, the controller 30 instructs the drive circuitry 34 to continue sonicating the target region 24 (step 47).

The steps (43, 45, 47, 48, 50, and 52) of treatment process 41 are not confined to the order as shown. The steps could be, for example, performed in a different order or in parallel with other steps. For example, the guiding procedure (step 45) may be performed immediately before, after, or in parallel with one or more steps (43, 47, 48, 50, and 52). Furthermore, any one or more steps of the treatment process 41 could be performed multiple times. For example, the administration of the exogenous agent (step 43) could be performed immediately before the array 20 is guided to the target region 24 (step 45) and again immediately after the target region 24 is sonicated (step 47).

Figure 4:
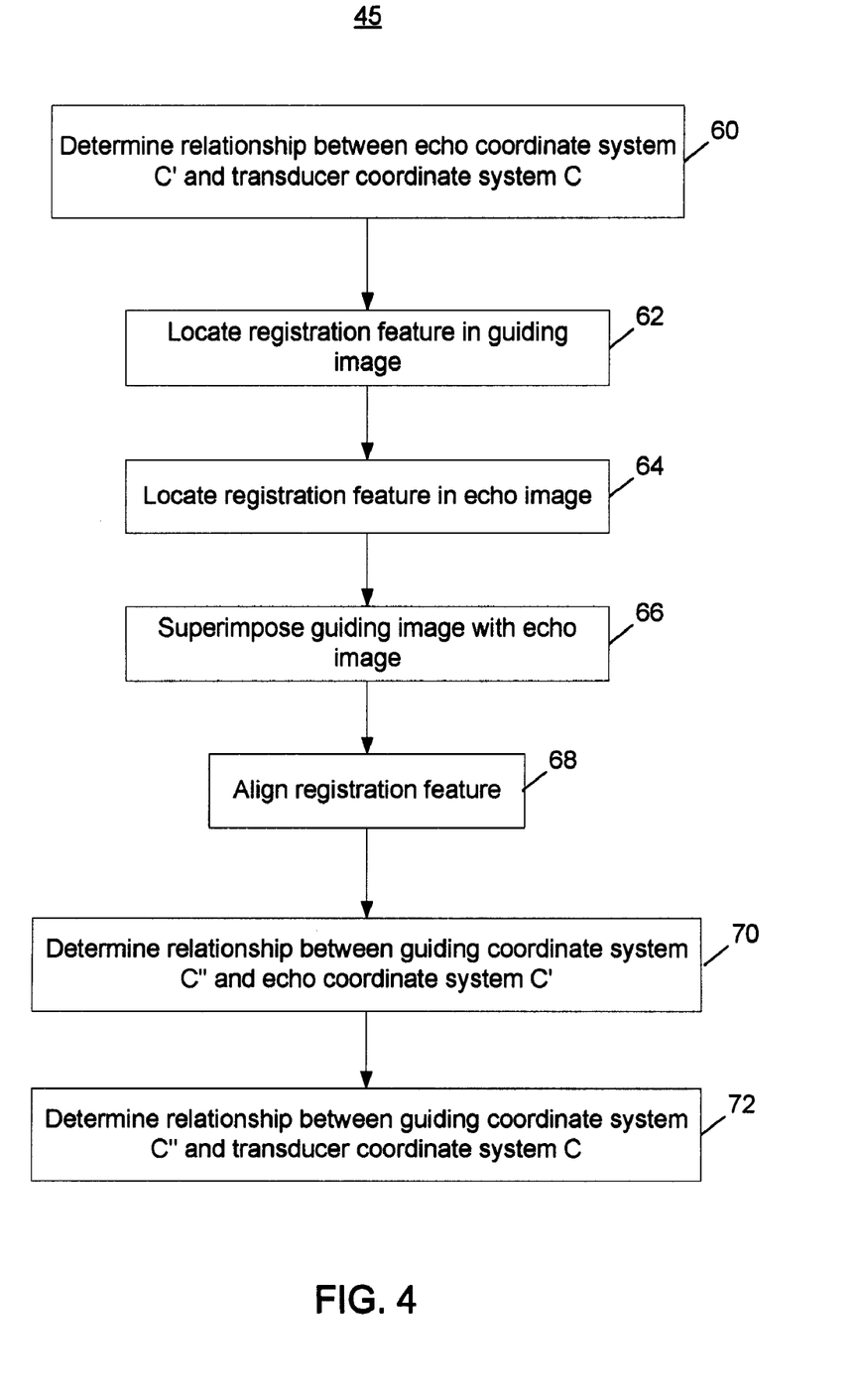
FIG. 4 is a flow chart of a process for guiding ultrasonic radiation to a target location.
Figure 5:
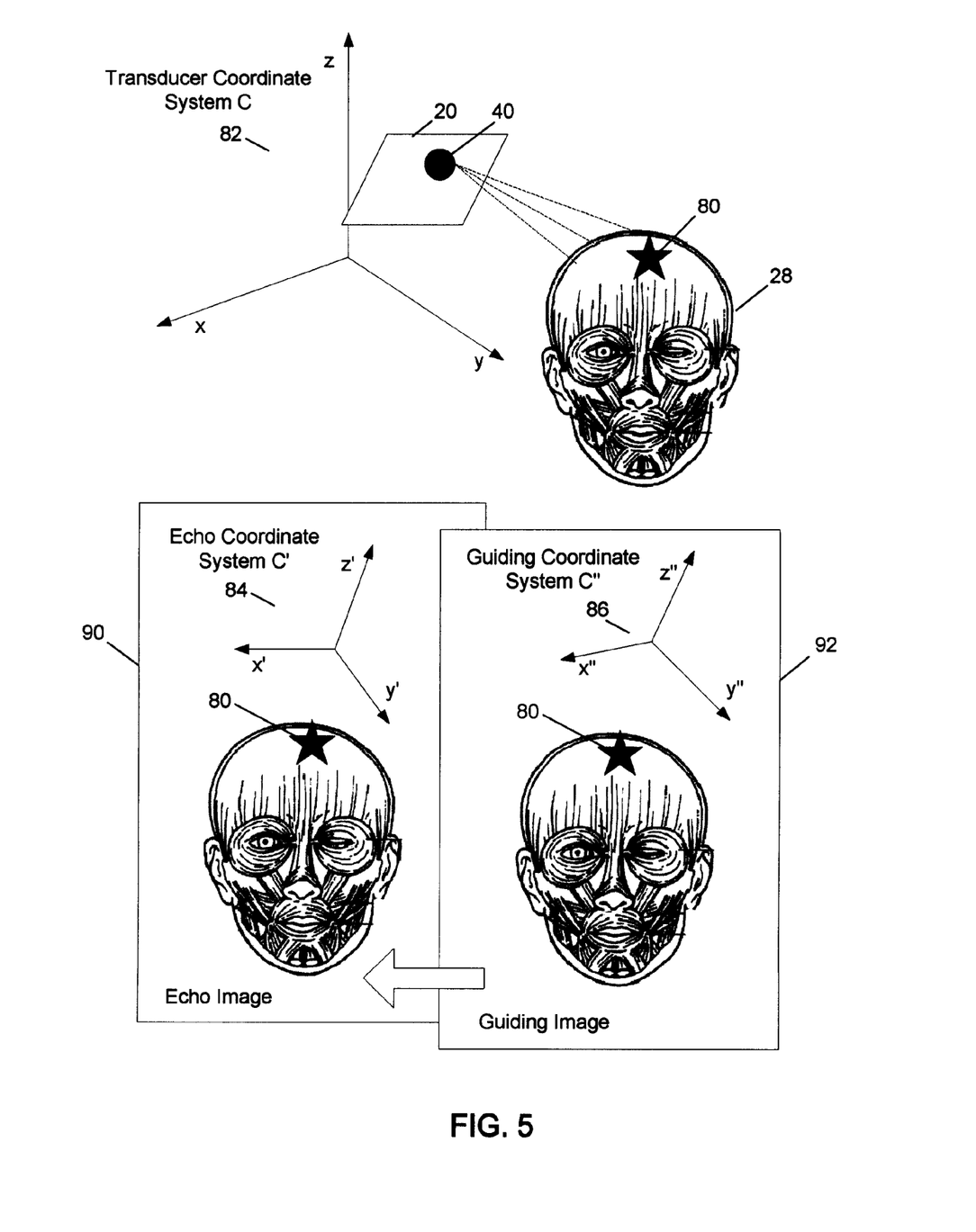
FIG. 5 depicts a procedure for registering the coordinate system of a transducer in an ultrasound array with the coordinate system of a guiding image.

FIG. 4 and FIG. 5 depict the guiding procedure (step 45) of the treatment process 41 in more detail. Before the guiding procedure (step 45) is initiated, an echo image 90 and a guiding image 92 of the patient's skull is obtained. As seen in FIG. 5, the echo image 90 is registered to an echo coordinate system C' 84 and the guiding image 92 is registered to a guiding coordinate system C" 86. The guiding image 92 may be, for example, a CT image or an MRI image.

The echo image 90 is formed by measuring the return echoes of ultrasound directed from each transducer 40 onto the skull. The location of a transducer 40 with respect to the skull may be determined from the return echo. The location includes the distance and angle between the transducer 40 and the skull.

Referring back to FIG. 4, the guiding procedure (step 45) continues with the determination of a relationship between the echo coordinate system C' 84 and the transducer coordinate system C 82 (step 60). Because both positions of the transducers 40 with respect to the patient's skull and the coordinates of the patient's skull are known, the location of the transducers 40 with respect to the echo coordinate system C' 84 may also be determined. A relationship that maps the echo coordinate system C' 84 to the transducer coordinate system C 82 is derived. The relationship may be expressed as a transformation matrix that maps the echo coordinate system C' 84 to the transducer coordinate system C 82.

Referring to FIG. 5, a registration feature 80 is located in the echo image 90 and the guiding image 92 (steps 62 and 64). In particular, the registration feature 80 is a conspicuous landmark on the skull that may be easily identified in both the echo image 90 and the guiding image 92. For example, the registration feature 80 may be a noticeable irregularity of the skull, such as an indentation or a nodule. The registration feature 80 may also be the top of the skull itself, or any other location on the skull.

The echo image 90 and the guiding image 92 are superimposed (step 66) and positioned to align the registration feature 80 (step 68) of both images 90 and 92. The alignment may be improved using algorithms to find a best correlation between the echo image 90 and the guiding image 92. From the alignment of the superimposed images, the relationship between the guiding coordinate system C" 86 and the echo coordinate system C' 84 is determined (step 70). The relationship may be expressed as a transformation matrix that maps the guiding coordinate system C" 86 to the echo coordinate system C' 84. Combining the relationship between the guiding coordinate system C" 86 and the echo coordinate system C' 84 with the relationship between the echo coordinate system C' 84 and the transducer coordinate system C 82, a relationship between the guiding coordinate system C" 86 and the transducer coordinate system C 82 may be established (step 72). The relationship between the guiding coordinate system C" 86 and the transducer coordinate system C 82 may be expressed as a transformation matrix composed of a first transformation matrix relating the echo coordinate system C' 84 and the transducer coordinate system C 82 and a second transformation matrix relating the guiding coordinate system C" 86 and the echo coordinate system C' 84.

Using the relationship for converting the guiding coordinate system C" 86 to the transducer coordinate system C 82, the guiding image 90 may be used as a "road map" to navigate the focal region of the ultrasonic radiation 22 to a target region 24 in a patient's brain. For example, a target region 24 may be located in the guiding image 90 at a particular set of image coordinates of the guiding coordinate system C" 86. Using the coordinate system transformations discussed above to convert the guiding coordinate system C" 86 to the transducer coordinate system C 82, the controller 30 may calculate the location of the transducer 40 relative to that of the target region 24. The controller 30 would then direct the transducer 40 to sonicate the target region 24 accordingly. During the treatment process 41, the echo image 90 may be updated periodically to account for any change in the positions of either the patient's skull or the array 20.

A number of embodiments of the invention have been described. Nevertheless, it will be understood that various modifications may be made without departing from the spirit and scope of the invention. For example, the system 10 could be used to open any blood-organ barrier, or for any other intervention or diagnostic procedure requiring ultrasound deposition. Accordingly, other embodiments are within the scope of the following claims.

What is claimed is:

1. A method for opening a blood-brain barrier in a subject, the method comprising:
   identifying a target region associated with a blood-brain barrier in a subject;
   controlling a focal region associated with ultrasonic radiation to overlap the target region;
   directing, through the subject's skull, ultrasonic radiation having a frequency below 500 kHz to the target region within the focal region to open the blood brain barrier at the target region;
   adjusting the frequency with a controller such that wavefronts of the ultrasonic radiation remain essentially unchanged while passing through the skull;
   while tissue in the target is undergoing sonication, monitoring acoustic emissions acquired by an acoustic detector and resulting from interaction between the ultrasonic radiation and gaseous bubbles triggered by the ultrasonic radiation at the target region; and
   analyzing the acoustic emissions using a processing system to track and adaptively control the progress of sonication by:
      determining a physical state of the blood-brain barrier; and
      stopping the ultrasonic radiation if an opening in the blood-brain barrier is detected.

2. The method of claim 1, wherein directing the ultrasonic radiation further comprises generating the ultrasonic radiation using an array of ultrasound transducers.

3. The method of claim 2, further comprising configuring the array to have fewer than 5000 ultrasound transducers.

4. The method of claim 2, further comprising:
   configuring the array to have approximately 1000 ultrasound transducers operable to emit the ultrasonic radiation at a frequency of approximately 250 kHz.

5. The method of claim 2, further comprising: covering a portion of the skull with the array.

6. The method of claim 5, further comprising configuring the array to assume a hemispherical shape.

7. The method of claim 1, wherein adjusting the frequency comprises selecting a frequency having a wavelength that minimizes focal distortion generated by irregularities in regions surrounding the target region.

8. The method of claim 1, wherein adjusting the frequency comprises lowering the frequency until a shape and location of the focal region conforms to a shape and location of the target region.

9. The method of claim 1, wherein adjusting the ultrasonic radiation comprises selecting the frequency to be between approximately 100 kHz and 400 kHz.

10. The method of claim 1, wherein directing the ultrasonic radiation comprises generating ultrasonic radiation with a time averaged power of approximately 10 mW and a pressure amplitude of approximately 0.3 MPa within the focal region.

11. The method of claim 1, wherein identifying the target region associated with the blood-brain barrier includes locating the target region using a guiding image of the subject's skull; and
   wherein controlling the focal region includes:
      determining a relationship between a coordinate system of a transducer through which the ultrasonic radiation is emitted and a coordinate system of the guiding image; and
      navigating the focal region of the ultrasonic radiation to the target region based on the relationship.

12. The method of claim 1, wherein analyzing the acoustic emissions comprises analyzing acoustic data resulting from interaction between the ultrasonic radiation and the gaseous bubbles.

13. The method of claim 1, wherein analyzing the acoustic emissions comprises comparing monitored acoustic emissions with data indicative of an opened.

14. The method of claim 1, wherein adjusting the frequency further comprises adjusting the frequency to match a resonant frequency of the gaseous bubbles.

15. The method of claim 1, further comprising:
   ceasing emission of the ultrasonic radiation to the target region if the physical state of the blood-brain barrier indicates an opened state.

16. The method of claim 1, where adjusting the focal region includes:
   measuring return echoes of ultrasonic radiation directed to a skull associated with the blood-brain barrier to generate one or more echo coordinates;
   identifying one or more transducer coordinates associated with one or more transducers through which the ultrasonic radiation is emitted;
   generating one or more guiding coordinates using a guiding image of the skull; and
   adjusting the focal region based on the one or more echo coordinates, the one or more transducer coordinates and the one or more guiding coordinates.

17. A system for opening a blood-brain barrier in a subject, the system comprising:
   a controller for identifying a target region in a subject and controlling a focal region associated with ultrasonic radiation to overlap the target region;
   an ultrasound source for directing the ultrasonic radiation having a frequency below 500 kHz to the target region within the focal region to open the blood-brain barrier at the target region;
   an acoustic detector for receiving acoustic emissions resulting from interaction between the ultrasonic radiation and gaseous bubbles triggered by the ultrasonic radiation at the target region while tissue in the target region is undergoing sonication; and
   a processing system for analyzing the acoustic emissions to track and adaptively control the progress of sonication by determining a physical state of the blood-brain barrier and stopping sonication if an opening in the blood-brain barrier is detected.

18. The system of claim 17, wherein the ultrasound source comprises an array of ultrasound transducers coupled to the controller.

19. The system of claim 18, wherein the array is a hemispherical structure configured to surround the target region.

20. The system of claim 18, wherein the array comprises fewer than 5000 ultrasound transducers.

21. The system of claim 20, wherein the array further comprises approximately 1000 ultrasound transducers operable to emit the ultrasonic radiation at a frequency of approximately 250 kHz.

22. The system of claim 17, wherein the ultrasonic radiation has a frequency between approximately 100 kHz and 400 kHz.

23. The system of claim 17, wherein the ultrasonic radiation is emitted with a time averaged power of approximately 10 mW and a pressure amplitude of approximately 0.3 MPa within the focal region.

24. The system of claim 17 wherein the irregularities comprises one or more of bumps, indentations, and curvature anomalies of the subject's skull.

25. The system of claim 17, wherein the controller is further configured to:
    identify the target region using a guiding image of the subject's skull; and
    control the focal region by determining a relationship between a coordinate system of a transducer of the ultrasound source and a coordinate system of the guiding image and navigating the focal region of the ultrasonic radiation to the target region based on the relationship.

\* \* \* \* \*

UNITED STATES PATENT AND TRADEMARK OFFICE
CERTIFICATE OF CORRECTION

PATENT NO. : 7,674,229 B2   Page 1 of 1
APPLICATION NO. : 11/370094
DATED : March 9, 2010
INVENTOR(S) : Kullervo Hynynen and Nathan McDannold

It is certified that error appears in the above-identified patent and that said Letters Patent is hereby corrected as shown below:

Col. 8, line 19 (claim 13, line 3) delete "opened" and insert -- opened blood-brain barrier --, therefore.

Col. 9, line 12 (claim 24, line 1) delete "17" and insert -- 17, --, therefore.

Signed and Sealed this

Eleventh Day of May, 2010

David J. Kappos
*Director of the United States Patent and Trademark Office*